(12) United States Patent
Bratz et al.

(10) Patent No.: US 7,087,239 B2
(45) Date of Patent: Aug. 8, 2006

(54) CRYSTALLINE HYDRATES OF ANILIDE DERIVATIVES

(75) Inventors: Matthias Bratz, Limburgerhof (DE); August Wigger, Kemnath-Stadt (DE); Peter Erk, Frankenthal (DE); Hans Ziegler, Mutterstadt (DE); Thomas Kröhl, Mainz (DE); Karl-Friedrich Jäger, Limburgerhof (DE); Horst Mayer, Guaratingueta (BR)

(73) Assignee: BASF Aktiengesellschaft, Ludwigshafen (DE)

( * ) Notice: Subject to any disclaimer, the term of this patent is extended or adjusted under 35 U.S.C. 154(b) by 165 days.

(21) Appl. No.: 10/490,370

(22) PCT Filed: Sep. 14, 2002

(86) PCT No.: PCT/EP02/10320

§ 371 (c)(1),
(2), (4) Date: Mar. 23, 2004

(87) PCT Pub. No.: WO03/029219

PCT Pub. Date: Apr. 10, 2003

(65) Prior Publication Data

US 2004/0249164 A1 Dec. 9, 2004

(30) Foreign Application Priority Data

Sep. 25, 2001 (DE) ................. 101 47 034

(51) Int. Cl.
*A61N 25/00* (2006.01)
*A61N 43/40* (2006.01)
*C07D 211/72* (2006.01)
*C07D 211/78* (2006.01)
*C07C 239/00* (2006.01)

(52) U.S. Cl. ............ 424/405; 504/244; 546/316; 546/324; 564/182

(58) Field of Classification Search ............ 546/316, 546/324; 504/244; 424/405; 564/182
See application file for complete search history.

(56) References Cited

U.S. PATENT DOCUMENTS

| 5,330,995 A | 7/1994 | Eicken et al. |
| 5,438,070 A | 8/1995 | Eicken et al. |
| 5,480,897 A | 1/1996 | Eicken et al. |
| 5,556,988 A | 9/1996 | Eicken et al. |
| 5,589,493 A | 12/1996 | Eicken et al. |
| 5,672,564 A | 9/1997 | Wigger et al. |
| 6,350,765 B1 | 2/2002 | Schelberger et al. |

FOREIGN PATENT DOCUMENTS

| EP | 0545099 | * | 6/1993 |
| WO | 95/15690 | | 6/1995 |
| WO | 99/31979 | | 7/1999 |

OTHER PUBLICATIONS

Derwent Abst. 95-216234/29.

* cited by examiner

*Primary Examiner*—Cecilia J. Tsang
*Assistant Examiner*—Binta Robinson
(74) *Attorney, Agent, or Firm*—Novak Druce & Quigg, LLP; Jason D. Voight (57) ABSTRACT

The present invention relates to crystalline hydrates of substituted anilide derivatives, to their preparation, and to their use for controlling phytopathogenic fungi or undesired attack by insects or mites and/or for regulating the growth of plants.

14 Claims, 6 Drawing Sheets

CRYSTALLINE HYDRATES OF ANILIDE DERIVATIVES

The present invention relates to crystalline substituted anilide derivatives of the formula I (I)

in which
A is (A1)

or (A2)

$R^1$ is phenyl which is substituted by halogen,
$R^2$ is methyl, difluoromethyl, trifluoromethyl, chlorine, bromine or iodine,
$R^3$ is trifluoromethyl or chlorine, which are present as hydrates. The present invention furthermore encompasses the preparation of suspension concentrates and suspoemulsions using the abovementioned active ingredient hydrate and methods for controlling phytopathogenic fungi or undesired attack by insects or mites and/or for regulating the growth of plants via dilution of the abovementioned formulations.

The fungicidal action of pyridylamides of the formula I (A=A2), a class of essentially water-insoluble compounds, and methods for their preparation are known (EP-A2 545099). These compounds can be obtained industrially by crystallization from an organic solvent.

If it is desired to formulate water-insoluble compounds for the purpose of applying them in liquid form to the pests or plants in question, there are essentially two possibilities:
1. The active ingredient is formulated as an emulsion concentrate (EC).
2. The active ingredient is formulated as an aqueous suspension concentrate (SC). Here, an organic phase which may optionally comprise further adjuvants or active ingredients may be added to the SC. The formulation prepared is termed a suspoemulsion (SE).

It is advantageous to provide aqueous formulations, taking into consideration the pollution of the environment by organic solvents as are used in large amounts in ECs.

SCs consist essentially of an aqueous phase in which the active ingredient, besides adjuvants, is suspended. The preparation of SCs is known to the skilled worker. For example, SCs can be prepared by milling the abovementioned active ingredient in the presence of various adjuvants and water as continuous medium (Mollet, H. and Grubemann, A. "Formulierungstechnik" [Formulation technology], WILEY-VCH, 2000, p. 133 et seq.).

The term adjuvants is understood as meaning inn the present context formulation auxiliaries such as surfactants, thickeners, solvents, antifoams, bactericides and antifreeze agents.

Said SCs can be used for the preparation of SEs. This is the case as a rule when the active ingredient(s) present in the suspension is/are to be combined with liquid active ingredients which are not miscible with water, or with oily active ingredients or with an organic active ingredient solution of a water-insoluble active ingredient in a readymix. The preparation of SEs is known to the skilled worker; for example, SEs can be prepared by the method described in EP-A 707445.

When the abovementioned SCs are prepared, it is necessary to grind the active ingredient as finely as possible in the presence of water and further adjuvants.

In the case of the abovementioned anilide derivatives, surprisingly, this is not possible since they form a loamy solid during the preparation of an SC, which does not allow the milling procedure to be continued.

It is an object of the present invention to modify the active ingredient in such a way that it can be ground with adjuvants in the presence of water.

We have found that this object is achieved by providing the corresponding hydrates of anilide derivatives. Surprisingly, we have found that, in contrast to the anhydrates, the hydrates can be ground without problems.

The present invention claims hydrates of anilide derivatives of the formula I:

(I)

in which
A is (A1)

(A2)

$R^1$ is phenyl which is substituted by halogen,
$R^2$ is methyl, difluoromethyl, trifluoromethyl, chlorine, bromine or iodine,
$R^3$ is trifluoromethyl or halogen, the linkage of A1 in position 2 and of A2 in position 3 relative to the parent compound I being preferred.

Especially preferred in this context are hydrates of nicotinanilide derivatives of the formula II:

(II)

in which
R¹ is phenyl which is substituted by halogen, and
R³ is halogen.

The phenyl radical is preferably monosubstituted to trisubstituted by halogen.

Halogen is understood as meaning, in the present context, fluorine, chlorine, bromine or iodine, especially preferably chlorine.

The compound 2-chloro-N-(4'-chlorobiphenyl-2-yl)nicotinamide is very specially preferred.

Especially preferred among the abovementioned hydrates of the anilide derivatives are the corresponding monohydrates.

The preparation of the amide compounds of the formula I or II is known, for example, from EP-A-545 099 or EP-A-589 301 or can be effected by analogous methods.

The present invention furthermore relates to methods for the preparation of the abovementioned hydrates.

In one embodiment (method 1), the method encompasses the following steps:
a) dissolving the anhydrate of I in a water-soluble organic solvent, and
b) precipitating the hydrate of I by addition of water.

The term water-soluble solvent refers in this context to a solvent which is soluble in water to at least 5%.

The ratio between water and organic phase in step a) of the abovementioned method is generally 1:10 to 10:1, preferably 1:3 to 3:1.

Water-soluble organic solvents which can be used in this context are cyclic ethers such as dioxane or tetrahydrofuran, alcohols such as methanol, ethanol, propanol, butanol or pentanol, and dimethylformamide or N-methylpyrrolidone, or mixtures of the above. The use of tetrahydrofuran is preferred.

In a further embodiment (method 2), the method encompasses the following steps:
a) mixing an organic solution comprising the anhydrate of I with water,
b) heating the mixture prepared in step a) at a temperature of 30–150° C.,
c) cooling the resulting solution.

In step a) of the abovementioned method, the ratio between water and organic phase is generally 10:1 to 1:10, preferably 1:3 to 3:1.

Organic solvents which can be used in this context are cyclic ethers such as dioxane or tetrahydrofuran, ketones such as acetone, cyclohexanone or MEK, or aromatic solvents such as benzene, toluene, xylene or solvents such as dimethylformamide or N-methylpyrrolidone, or mixtures of the above.

In a preferred embodiment of method 2, the solution in step b) is incubated at a temperature of preferably 30–70° C., especially preferably 30–60° C., and subsequently suitably cooled.

In a further embodiment (method 3), the method encompasses the following steps:
a) mixing the solid anhydrate of I with water,
b) heating the mixture prepared in step a) at a temperature of 30–150° C. until the anhydrate has been converted into the hydrate, or
c) incubating the mixture prepared in step a) with exposure to shearing forces until the anhydrate has been converted into the hydrate.

In a preferred embodiment of the abovementioned method, the solution in step b) is incubated at a temperature of preferably 30–70° C., especially preferably 30–60° C., and subsequently suitably cooled.

The incubation period in step b) is from 30 minutes to 48 hours. At least 50%, preferably at least 70%, of the anhydrate is converted into the hydrate.

The incubation in step c) is carried out over a period of at least 30 minutes to 48 hours.

The exposure of the mixture to strong shearing forces, which is described in step c), can be effected by milling in suitable mills. Mills with a short residence time of the product, such as rotor-stator mills, have proved to be particularly advantageous in this context.

In both of the abovementioned methods, the conversion rate of anhydrate into the hydrate can be monitored by means of a suitable analytical method, such as, for example, IR spectroscopy or X-ray powder diffractometry.

The conversion of hydrate/anhydrate can be quantified by IR, for example by the shift of characteirstic bands (for example C=O stretching vibration). Thus, for example, the C=O stretching vibration shifts from 1650 cm$^{-1}$ to 1660 cm$^{-1}$ from 2-chloro-N-(4'-chlorobiphenyl-2-yl)nicotinamide anhydrate to 2-chloro-N-(4'-chlorobiphenyl-2-yl)nicotinamide monohydrate. The disappearance of the band at 1650 cm$^{-1}$ thus indicates complete conversion of the anhydrate into the hydrate.

In method 3, the preparation of the respective hydrate by one of the abovementioned methods can even be carried out in the presence of adjuvants ("direct method").

The present invention also relates to suspoemulsions (SE) or suspension concentrates (SC) comprising, as essential component, the hydrate of an active ingredient I, with A preferably being A2.

For the preparation of SCs, for example, the hydrate of the anilide derivative is milled in water in the presence of surfactants, and if appropriate of further adjuvants.

In a possible embodiment of the abovementioned preparation procedure, the surfactants are first homogenized together with the antifreeze agent and water, and a anilide derivative hydrate which has been prepared by a method according to the invention is then added. The resulting mash can subsequently be comminuted directly in a mill, for example a stirred ball mill. Other suitable mills are mentioned in Mollet, H. and Grubemann, A. "Formulierungstechnik" [Formulation technology], WILEY-VCH, 2000. To achieve the desired fineness, it may be necessary to repeat the milling step several times.

When the desired particle size distribution of preferably 40% smaller than 2 microns and 100% smaller than 12 microns has been achieved, thixotropic agents may, as a rule, be added to the suspension.

In a preferred embodiment, the hydrate is prepared via steps a) and b) of method 3, suitable adjuvants previously having been added to the mixture as it is produced. Directly thereafter, the mixture prepared is milled finely as described above. milling in a stirred ball mill is especially preferred in this context.

Surfactants which are suitable for the above mentioned formulations are ionic surfactants and nonionic surfactants, preferably mixtures of the two.

Examples of suitable ionic surfactants are alkylarylsulfonates, phenylsulfonates, alkyl sulfates, alkylsulfonates, alkyl ether sulfates, alkylaryl ether sulfates, alkyl polyglycol ether phosphates, polyaryl phenyl ether phosphates, alkylsulfosuccinates, olefinsulfonates, paraffinsulfonates, petroleum sulfonates, taurides, sarcosides, fatty acids, alkylnaphthalenesulfonic acids, naphthalenesulfonic acids, lignosulfonic acids, condensates of sulfonated naphthalenes with formaldehyde or with formaldehyde and phenol and, if appropriate, urea, lignin-sulfite waste liquors, including their alkali metal salts, alkaline earth metal salts, ammonium salts and amine salts, alkyl phosphates, quaternary ammonium compounds, betaines and their mixtures, and also polycarboxylates such as, for example, polyacrylates, maleic anhydride/olefin copolymers (for example Sokalan®CP9, BASF).

Preferred are condensates of sulfonated naphthalenes or phenols with formaldehyde and, if appropriate, urea, which are present as water-soluble salts such as, for example, as the sodium salt, such as naphthalenesulfonic acid/formaldehyde condensates, or condensates of phenolsulfonic acid, formaldehyde and urea (for example compounds such as Wettol®D1, Tamol®NH, Tamol®NH by BASF or Morwet®D425 by Witco).

Examples of suitable nonionic surfactants are alkylphenol alkoxylates, alcohol alkoxylates, fatty amine alkoxylates, polyoxyethylene glycerol fatty acid esters, castor oil alkoxylates, fatty acid alkoxylates, fatty acid amide alkoxylates, fatty acid polydiethanolamides, lanolin ethoxylates, fatty acid polyglycol esters, isotridecyl alcohol, fatty acid amides, methylcellulose, fatty acid esters, silicone oils, alkyl polyglycosides, glycerol fatty acid esters, polyethylene glycol, polypropylene glycol, polyethylene glycol/polypropylene glycol block copolymers, polyethylene glycol alkyl ethers, polypropylene glycol alkyl ethers, polyethylene glycol/polypropylene glycol ether block copolymers, and mixtures of these.

Preferred are polyethylene glycol/polypropylene glycol block copolymers, polyethylene glycol alkyl ethers, polypropylene glycol alkyl ethers, polyethylene glycol/polypropylene glycol ether block copolymers (for example compounds of the Pluronic® series by BASF), fatty acid alcohol alkoxyates (for example compounds of the Plurafac® series by BASF, Atlas®G5000 by Uniqema or Witoconol® NS500 by Crompton/Witco) and mixtures of these.

Preferred mixtures of ionic and nonionic surfactants are composed of polyethylene glycol/polypropylene glycol ether block copolymers and/or fatty acid alkoxylates together with condensates of sulfonated phenols with urea and formaldehyde or naphthalenesulfonic acid/formaldehyde condensates (for example compounds such as Wettol®D1, Tamol®NN, Tamol®NH by BASF or Morwet®D425 by Witco).

Viscosity-regulating additives which are suitable for the abovementioned formulation types are compounds which impart pseudoplastic flow behavior to the formulation, i.e. high viscosity in the state of rest and low viscosity in the state of motion.

Examples of suitable compounds are polysaccharides or organic sheet minerals such as xanthan gum (Kelzan® by Kelco), Rhodopol® 23 (Rhône-Poulenc) or Veegum® (R. T. Vanderbilt) or Attaclay® (Engelhardt).

Antifoams which are suitable for the formulations according to the invention are, for example, silicone emulsions (such as, for example, Silikon® SRE, by Wacker or Rhodorsil® by Rhodia), long-chain alcohols, fatty acids, organofluorine compounds and mixtures of these.

Bactericides may be added to stabilize the aqueous fungicide formulation. Examples of suitable bactericides are Proxel® by ICI or Acticide® RS by Thor Chemie and Kanthon® MK by Rohm & Haas.

Examples of suitable antifreeze agents are ethylene glycol, propylene glycol or glycerol.

To widen the spectrum of action or achieve specific effects, for example, the additional protection against insects, arachnids or mites, the abovementioned formulations can be combined with further agrochemical active ingredients which, in the latter case, can be incorporated together with suitable additives. The term additive refers in this context to a selection of the abovementioned surfactants and other adjuvants. In the case of an SC formulation, additional active ingredients can be dissolved in the aqueous phase or suspended in finely-ground form. In the case of an SE formulation, the SC according to the invention comprises a further active ingredient emulsified in liquid or dissolved form in the formulation, in addition to the suspended active ingredient.

Substances which are suitable for the organic phase of the SE formulations according to the invention are alkylbenzene-based aromatic hydrocarbons such as, for example, xylene, toluene, trimethylbenzene, methylethylbenzene, dimethylethylbenzene, diethylbenzene, tetramethylbenzene and pentamethylbenzene. Especially suitable are mixtures of aromatic hydrocarbons like the solvents which are commercially available under the names Solvesso® (manufacturer: Esso) or Shellsol® (manufacturer: Shell). Solvents on a purely aliphatic basis which may be used are liquid paraffin (for example Linpar®: $C_{14}$–$C_{17}$-hydrocarbon fraction from Wintershall), but also native oils such as rapeseed oil and soya oil, as long as they are capable of dissolving the active ingredient sufficiently. Moreover, esters of natural and synthetic fatty acids or polycarboxylic acids and mixtures of these (for example acetates such as methyl acetate, ethyl acetate, propyl acetate, but also acetates of higher alcohols ($C_5$–$C_{20}$-alcohols), dialkyl adipate, alkyl glutarate or alkyl citrate) may be used.

For the purposes of the present invention, the term agrochemical active ingredient is understood as meaning not only fungicides, but also insectides and growth regulators.

The following list of fungicides identifies possible active ingredients, but not by way of limitation:

sulfur, dithiocarbamates and their derivatives, such as iron (III)
dimethyldithiocarbamate, zinc dimethyldithiocarbamate, zinc
ethylenebisdithiocarbamate, manganese ethylenebisdithiocarbamate,
manganese zinc ethylenediaminebisdithiocarbamate,
tetramethylthiuram disulfide, ammonia complex of zinc (N,N-ethylenebisdithiocarbamate), ammonia complex of zinc
(N,N'-propylenebisdithiocarbamate), zinc
(N,N'-propylenebisdithiocarbamate),
N,N'-polypropylenebis(thiocarbamoyl) disulfide;

nitro derivatives, such as dinitro(1-methylheptyl)phenyl crotonate, 2-sec-butyl-4,6-dinitrophenyl 3,3-dimethylacrylate,
2-sec-butyl-4,6-dinitrophenylisopropyl carbonate, diisopropyl
5-nitroisophthalate;

heterocyclic substances, such as 2-heptadecyl-2-imidazoline acetate, 2,4-dichloro-6-(o-chloroanilino)-s-triazine, O,O-diethyl phthalimidophosphonothioate, 5-amino-1-[bis(dimethylamino)phosphinyl]-3-phenyl-1,2,4-triazole, 2,3-dicyano-1,4-dithioanthraquinone, 2-thio-1,3-dithiolo[4,5-b]quinoxaline, methyl 1-(butylcarbamoyl)-2-benzimidazolecarbamate, 2-methoxycarbonylaminobenzimidazole, 2-(2-furyl)-benzimidazole, 2-(4-thiazolyl)benzimidazole, N-(1,1,2,2-tetrachloroethylthio)tetrahydrophthalimide, N-trichloromethylthiotetrahydrophthalimide, N-trichloromethylthiophthalimide, N-dichlorofluoromethylthio-N',N'-dimethyl-N-phenylsulfamide, 5-ethoxy-3-trichloromethyl-1,2,3-thiadiazole, 2-thiocyanatomethylthiobenzothiazole, 1,4-dichloro-2,5-dimethoxybenzene, 4-(2-chlorophenylhydrazono)-3-methyl-5-isoxazolone, pyridine-2-thiol 1-oxide, 8-hydroxyquinoline or its copper salt, 2,3-dihydro-5-carboxanilido-6-methyl-1,4-oxathiine, 2,3-dihydro-5-carboxanilido-6-methyl-1,4-oxathiine 4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, N-cyclohexyl-2,5-dimethylfuran-3-carboxamide, N-cyclohexyl-N-methoxy-2,5-dimethylfuran-3-carboxamide, 2-methylbenzanilide, 2-iodobenzanilide, N-formyl-N-morpholine-2,2,2-trichloroethyl acetal, piperazine-1,4-diylbis-1-(2,2,2-trichloroethyl)formamide, 1-(3,4-dichloroanilino)-1-formylamino-2,2,2-trichloroethane, 2,6-dimethyl-N-tridecylmorpholine or its salts, 2,6-dimethyl-N-cyclododecylmorpholine or its salts, N-[3-(p-tert-butylphenyl)-2-methylpropyl]-cis-2,6-dimethylmorpholine, N-[3-(p-tert-butylphenyl)-2-methylpropyl] piperidine, 1-[2-(2,4-dichlorophenyl)-4-ethyl-1,3-dioxolan-2-ylethyl]-1H-1,2,4-triazole, 1-[2-(2,4-dichlorophenyl)-4-n-propyl-1,3-dioxolan-2-ylethyl]-1H-1,2,4-triazole, N-(n-propyl)-N-(2,4,6-trichlorophenoxyethyl)-N'-imidazolylurea, 1-(4-chlorophenoxy)-3,3-dimethyl-1-(1H-1,2,4-triazol-1-yl)-2-butanone, 1-(4-chlorophenoxy)-3,3-dimethyl-1-(1H-1,2,4-triazol-1-yl)-2-butanol, (2RS,3RS)-1-[3-(2-chlorophenyl)-2-(4-fluorophenyl)oxiran-2-ylmethyl]-1H-1,2,4-triazole, α-(2-chlorophenyl)-α-(4-chlorophenyl)-5-pyrimidinemethanol, 5-butyl-2-dimethylamino-4-hydroxy-6-methylpyrimidine, bis(p-chlorophenyl)-3-pyridinemethanol, 1,2-bis(3-ethoxycarbonyl-2-thioureido)benzene, 1,2-bis(3-methoxycarbonyl-2-thioureido)benzene, anilinopyrimidines such as N-(4,6-dimethylpyrimidin-2-yl)aniline, N-[4-methyl-6-(1-propynyl)pyrimidin-2-yl]aniline, N-[4-methyl-6-cyclopropylpyrimidin-2-yl]aniline, phenylpyrroles such as 4-(2,2-difluoro-1,3-benzodioxol-4-yl)pyrrole-3-carbonitrile, cinnamamides such as 3-(4-chlorophenyl)-3-(3,4-dimethoxy-phenyl)acryloylmorpholine, and a variety of fungicides such as dodecylguanidine acetate, 3-[3-(3,5-dimethyl-2-oxycyclohexyl)-2-hydroxyethyl]glutarimide, hexachlorobenzene, methyl N-(2,6-dimethylphenyl)-N-(2-furoyl)-DL-alaninate, DL-N-(2,6-dimethylphenyl)-N-(2'-methoxyacetyl)alanine methyl ester, N-(2,6-dimethylphenyl)-N-chloroacetyl-D,L-2-aminobutyrolactone, DL-N-(2,6-dimethylphenyl)-N-(phenylacetyl)alanine methyl ester, 5-methyl-5-vinyl-3-(3,5-dichlorophenyl)-2,4-dioxo-1,3-oxazolidine, 3-(3,5-dichlorophenyl)-5-methyl-5-methoxymethyl-1,3-oxazolidine-2,4-dione, 3-(3,5-dichlorophenyl)-1-isopropylcarbamoylhydantoin, N-(3,5-dichlorophenyl)-1,2-dimethylcyclopropane-1,2-dicarboximide, 2-cyano-[N-(ethylaminocarbonyl)-2-methoximino]acetamide, 1-[2-(2,4-dichlorophenyl)pentyl]-1H-1,2,4-triazole, 2,4-difluoro-α-(1H-1,2,4-triazolyl-1-methyl)benzhydryl alcohol, N-(3-chloro-2,6-dinitro-4-trifluoromethylphenyl)-5-trifluoro-methyl-3-chloro-2-aminopyridine, 1-((bis(4-fluorophenyl)methylsilyl)methyl)-1H-1,2,4-triazole, N-dimethyl-5-chloro-2-cyano-4-p-tolylimidazole-1-sulfonamide, 3,5-dichloro-N-(3-chloro-1-ethyl-1-methyl-2-oxopropyl)-4-methyl benzamide.

Strobilurins such as methyl E-methoxyimino-[α-(o-tolyloxy)-o-tolyl]acetate, methyl E-2-{2-[6-(2-cyanophenoxy)pyrimidin-4-yloxy]phenyl}-3-methoxyacrylate (azoxystrobin), N-methyl-E-methoxyimino-[α-(2-phenoxyphenyl)]acetamide (metominostrobin), N-methyl-E-methoxyimino-[α-(2,5-dimethylphenoxy)-o-tolyl] acetamide, methyl E-2-{2-[(2-trifluoromethylpyridyl-6-)oxymethyl]phenyl}-3-methoxyacrylate, methyl (E,E)-methoximino-{2-[1-(3-trifluoromethylphenyl)ethylideneaminooxymethyl]phenyl}-acetate (trifloxystrobin), methyl N-(2-{[1-(4-chlorophenyl)-1H-pyrazol-3-yl]oxymethyl}phenyl)-N-methoxycarbamate.

The following list of insecticides identifies possible active ingredients, but not by way of limitation:

neonicotinoids/chloronicotinyl compounds (such as imidacloprid, acetamiprid, nitenpyram, thiacloprid, thiamethoxam, MIT-446 (terafuranitdine)

pyrroles (such as chlorphenapyr, fludioxonil)

organophosphates (such as acephate, azinphos-methyl, chlorpyrifos, dimethoate, disulfoton, fosthiazate, methamidophos, methidathion, methyl-parathion, oxydemeton-methyl, phorate, phosalone, phosmet, profenofos, trichlorfon, malathion, phosphamidon, monocrotophos, fenitrothion, diazinon, EPN)

carbamates (such as alanycarb, aldicarb, benfuracarb, carbofuran, carbosulfan, furathiocarb, methomyl, oxamyl, pirimicarb, thiodicarb, fenobucarb) pyrethroids (such as bifenthrin, cyfluthrin, cypermethrin, deltamethrin, ethofenprox, esfenvalerate, fenpropathrin, flucythrinate, fluvalinate, lambda-cyhalothrin, permethrin, pyrethrin I, pyrethrin II, silafluofen, tau-fluvalinate, tralomethrin, zeta-cypermethrin)

urea derivatives (such as diflubenzuron, flucycloxuron, flufenoxuron, hexaflumuron, lufenuron, novaluron, triflumuron juvenoids (such as buprofezin, diofenolan, fenoxycarb, pyriproxifen, methoxyfenozide, tebufenozide)

The following list of compounds with growth-regulatory activity identifies possible active ingredients, but not by way of limitation:

1-naphthylacetamide, 1-naphthylacetic acid, 2-naphthyloxyacetic acid, 3-CPA, 4-CPA, ancymidol, anthraquinone, BAP, butifos; tribufos, butralin, chlorflurenol, chlormequat, clofenacet, cyclanilide, daminozide, dicamba, dikegulac sodium, dimethipin, chlorfenethol, etacelasil, ethephon, ethychlozate, fenoprop, 2,4,5-TP, fluoridamid, flurprimidol, flutriafol, gibberellic acid, gibberellin, guazatin, imazalil, indolylbutyric acid, indolylacetic acid, karetazan, kinetin, lactidichlor-ethyl, maleic hydrazide, mefluidide, mepiquatchloride, naptalam, paclobutrazole, prohexadione-calcium, quinmerac, sintofen, tetcyclacis, thidiazuron, triiodobenzoic acid, triapenthenol, triazethan, tribufos, trinexapac-ethyl, uniconazole.

The present invention furthermore relates to a method of controlling phytopathogenic fungi or undesired attack by insects or mites and/or for regulating the growth of plants, which is based on suitably diluting an SC or SE formulation according to the invention and applying the dilute product to the respective pest or plant, it being possible for the SC or SE formulation in each case to comprise a further agrochemical active ingredient from among those mentioned above. The dilution rate depends on the nature of the active ingredient or the active ingredient combination.

Phytopathogenic fungi which can be controlled by the formulations according to the invention are understood as meaning, for example, the following species:

*Alternaria* species, *Podosphaera* species, *Sclerotinia* species, Physalospora canker on vegetables and fruit, *Botrytis cinerea* (gray mold) on strawberries, vegetables, ornamentals and grapevines, *Corynespora melonis* on cucumbers and strawberries; *Colletotrichum* species on cucumbers; *Diplocarpon rosae* on roses; *Elsinoe fawcetti* and *Diaporthe citri* on citrus fruit; *Sphaerotheca* species on cucumbers, cucurbits, strawberries and roses; *Cercospora* species on peanuts, sugar beet, egg plant and date plums; *Erysiphe cichoracearum* and *Sphaerotheca fuliginea* on cucurbits, *Leveiillina taurica* on pimento; *Mycosphaerella* species on apples and Japanese apricot; *Phyllactinia kakicola*, *Gloesporium kaki* on Japanese apricot; *Gymnosporangium yamadae*, *Leptotthrydium pomi*, *Podosphaera leucotricha* and *Gloedes pomigena* on apples; *Cladosporium carpophilum* on pears and Japanese apricot; *Phomopsis* species on pears; *Phytopora* species on citrus fruit, potatoes, onions; *Phytophthora infestans* on potatoes and tomatoes, *Erysiphe graminis* (powdery mildew) on cereals, *Fusarium* and *Verticillium* species on a variety of plants, *Glomerella cingulata* on tea; *Helminthosporium* species on cereals, *Mycosphaerella* species on bananas and peanuts, *Plasmopara viticola* on grapevines and grapefruits, *Peronospora* species on onions, spinach and chrysanthemums; *Phaeoisariopsis vitis* and *Spaceloma ampelina* on grapefruits; *Pseudocercosporella herpotrichoides* on wheat and barley, *Pseudoperonospora* species on hops and cucumbers, *Puccinia* species and *Typhula* species on cereals, *Pyricularia oryzae* on rice, *Rhizoctonia* species on cotton, rice and turf, *Septoria nodorum* on wheat, *Uncinula necator* on grapevine, *Ustilago* species on cereals and sugar cane, and also *Venturia* species (scab) on apples and pears.

Examples of insects which can be controlled by the formulations according to the invention are insects from the order Lepidoptera (butterflies and moths) for example *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithotis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni* and *Zeiraphera canadensis*, from the order Coleoptera (beetles), for example *Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrhynchus napi, Chaetocnema tibialis, Conoderus vespertinus, Crioceris asparagi, Diabrotica longicornis, Diabrotica 12-punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Otiorrhynchus sulcatus, Otiorrhynchus ovatus, Phaedon cochleariae, Phyllotreta chrysocephala, Phyllophaga sp., Phyllopertha horticola, Phyllotreta nemorum, Phyllotreta striolata, Popillia japonica, Sitona lineatus* and *Sitophilus granaria*, from the order of the Diptera (dipterans), for example *Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossina morsitans, Haematobia irritans, Haplodiplosis equestris, Hylemyia platura, Hypoderma lineata, Liriomyza sativae, Liriomyza trifolii, Lucilia caprina, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea* and *Tipula paludosa*, from the order Thysanoptera, for example *Frankliniella fusca, Frankliniella occidentalis, Frankliniella tritici, Scirtothrips citri, Thrips oryzae, Thrips palmi* and *Thrips tabaci*, from the order Hymenoptera, for example *Athalia rosae, Atta cephalotes, Atta sexdens, Atta texana, Hoplocampa minuta, Hoplocampa testudinea, Monomorium pharaonis, Solenopsis geminata* and *Solenopsis invicta*, from the order Heteroptera, for example *Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis* and *Thyanta perditor*, from the order Homoptera, for example *Acyrthosiphon onobrychis, Adelges laricis, Aphidula nasturtii, Aphis fabae, Aphis pomi, Aphis sambuci, Brachycaudus cardui, Brevicoryne brassicae, Cerosipha gossypii, Dreyfusia nordmannianae, Dreyfusia piceae, Dysaphis radicola, Dysaulacorthum pseudosolani, Empoasca fabae, Macrosiphum avenae, Macrosiphum euphorbiae, Macrosiphon rosae, Megoura viciae, Metopolophium dirhodum, Myzodes persicae, Myzus cerasi, Nilaparvata lugens, Pemphigus bursarius, Perkinsiella saccharicida, Phorodon humuli, Psylla mali, Psylla piri, Rhopalomyzus ascalonicus, Rhopalosiphum maidis, Sappaphis mala, Sappaphis mali, Schizaphis graminum, Schizoneura lanuginosa, Trialeurodes vaporariorum* and *Viteus vitifolii*, from the order Isoptera, for example *Calotermes flavicollis, Leucotermes flavipes, Reticulitermes lucifugus* and *Termes natalensis*, from the order Orthoptera, for example *Acheta domestica, Blatta orientalis, Blattella germanica, Forficula auricularia, Gryllotalpa gryllotalpa, Locusta migratoria, Melanoplus bivittatus, Melanoplus femur-rubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus* and *Tachycines asynamorus*, from the order Acari, for example *Amblyomma americanum, Amblyomma variegatum, Argas persicus, Boophilus annulatus, Boophilus decoloratus, Boophilus microplus, Brevipalpus phoenicis, Bryobia praetiosa, Dermacentor silvarum, Eotetranychus carpini, Eriophyes sheldoni, Hyalomma truncatum, Ixodes ricinus, Ixodes rubicundus, Ornithodorus moubata, Otobius megnini, Paratetranychus pilosus, Dermanyssus gallinae, Phyllocoptruta oleivora, Polyphagotarsonemus latus, Psoroptes ovis, Rhipicephalus appendiculatus, Rhipicephalus evertsi, Sarcoptes scabiei, Tetranychus cinnabarinus, Tetranychus kanzawai, Tetranychus pacificus, Tetranychus telarius* and *Tetranychus urticae*, from the order the nematodes, such as root-knot nematodes, for example *Meloidogyne hapla, Meloidogyne incognita, Meloidogyne javanica*, cyst nematodes, for example *Globodera rostochiensis, Heterodera avenae, Heterodera glycines, Heterodera schachtii, Heterodera trifolii*, stem eelworms and foliar nematodes, for example *Belonolaimus longicaudatus, Ditylenchus destructor, Ditylenchus dipsaci, Heliocotylenchus multicinctus, Longidorus elongatus, Radopholus similis, Rotylenchus robustus, Trichodorus primitivus, Tylenchorhynchus claytoni, Tylenchorhynchus dubius, Pratylenchus neglectus, Pratylenchus penetrans, Pratylenchus curvitatus* and *Pratylenchus goodeyi*.

Regulation of the growth of plants can be effected by the growth regulators which have already been mentioned further above or by using fertilizer.

A preferred embodiment of the abovementioned method is a method of controlling phytopathogenic fungi.

All of the abovementioned methods can be carried out by suitably diluting an SC or SE formulation according to the invention and applying the dilution to the respective pest or to the materials, plants, soil and seeds to be protected from the respective pests, it being possible for the respective SC or SE formulation additionally to comprise a further fungicidal active ingredient.

In this context, the compositions according to the invention or the substances can be applied pre-emergence or post-emergence. If the active ingredients in question are less well tolerated by specific crop plants, application techniques can be used in which the dilute SC or SE formulations are sprayed, with the aid of the spraying apparatus, in such a way that the agrochemical active ingredients come into as little contact as possible, if any, with the leaves of the sensitive crop plants while reaching the bare soil surface (post-directed, lay-by).

The application rates of active ingredient are from 0.001 to 3.0, preferably from 0.01 to 1.0, kg/ha, depending on the intended aim of the control measures, the season, the target plants and the growth stage.

In the following text, the method according to the invention is illustrated with reference to examples, but it is not limited thereto:

EXAMPLE 1

A) Preparation of the Anhydrate

2-Chloro-N-(4'-chlorobiphenyl-2-yl)nicotinamide was obtained at the end of the synthesis as hot xylenic solution. Upon cooling slowly, virtually all of the active ingredient crystallized from xylene. After filtration, residual xylene was removed by drying in a vacuum drying oven, whereby the active ingredient was obtained in the form of the anhydrate. The physical properties are compiled in Table 1.

B) Preparation of the hydrate 1 g of 2-chloro-N-(4'-chlorobiphenyl-2-yl)nicotinamide anhydrate 45 was dissolved in 20 ml of THF at 40° C. and the solution was then poured into 20 ml of water. The material which had precipitated was filtered off with suction and dried at 40° C. in a drying oven.

The physical properties of the 2-chloro-N-(4'-chlorobiphenyl-2-yl)nicotinamide monohydrate thus prepared are shown in Tabelle 1.

C) Analysis of the Conversion of Hydrate/Anhydrate

The IR spectra were recorded with an FT IR spectrometer. The samples were either prepared as KBr disks or measured using what is known as a single-reflexion diamond ATR measuring unit (Durascope, Resultec).

When the measurement was carried out using the single-reflexion diamond ATR measuring unit, the suspension comprising the solid to be tested was applied to a clay plate or filter paper. The solid which remained after removal of the water was subsequently applied to the single-reflexion diamond ATR measuring unit.

The IR spectra shown in FIGS. 1 to 4 (see also Table 1) furthermore illustrate the differences between 2-chloro-N-(4'-chlorobiphenyl-2-yl)nicotinamide monohydrate and 2-chloro-N-(4'-chlorobiphenyl-2-yl)nicotinamide anhydrate. Thus, IR spectroscopy can be used for monitoring the conversion rate.

Figure 1:
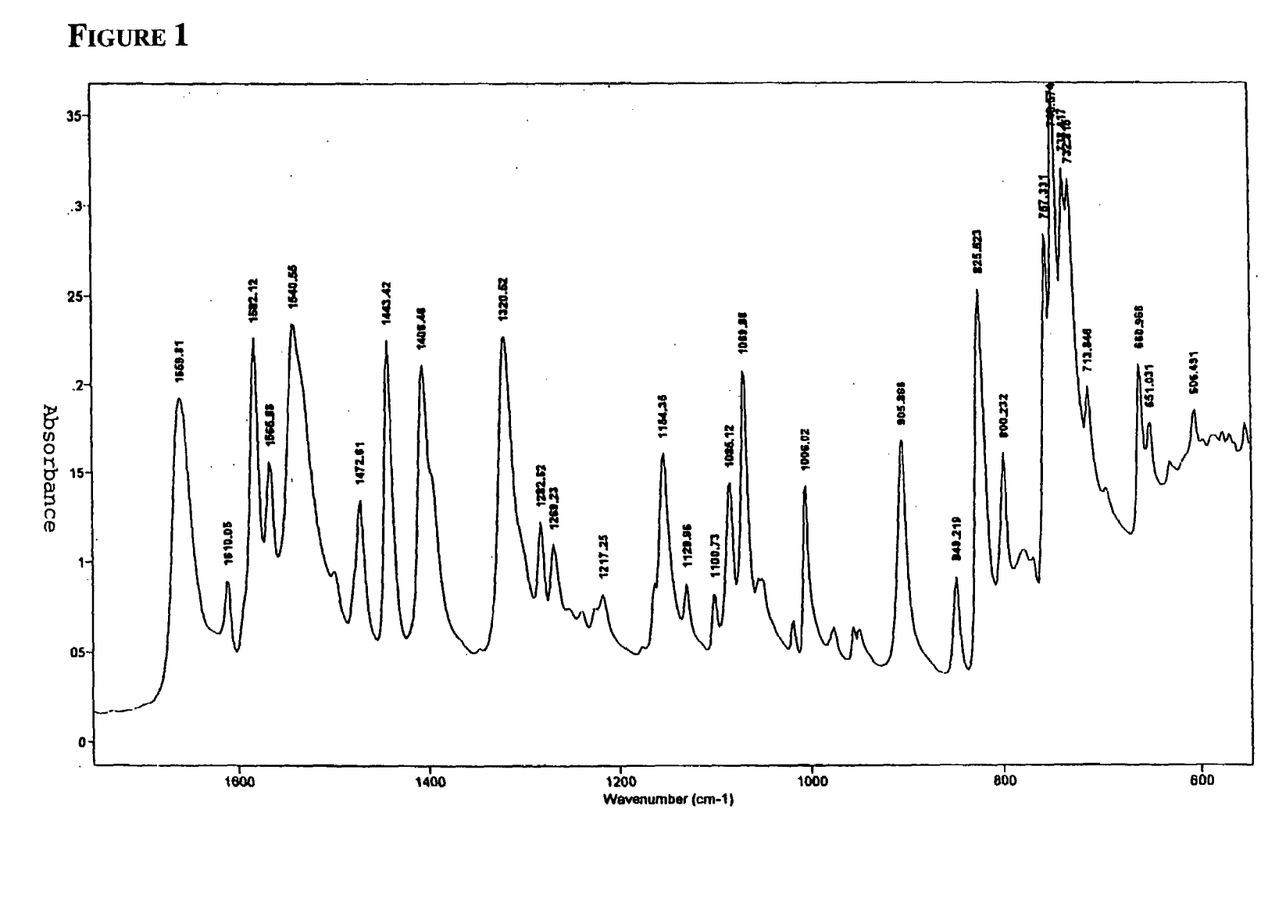
FIG. 1: IR spectrum of 2-Chloro-N-(4'-chloro-biphenyl-2-yl)-nicotinamidhydrat (1800 cm$^{-1}$ bis 600 cm$^{-1}$)
Figure 2:
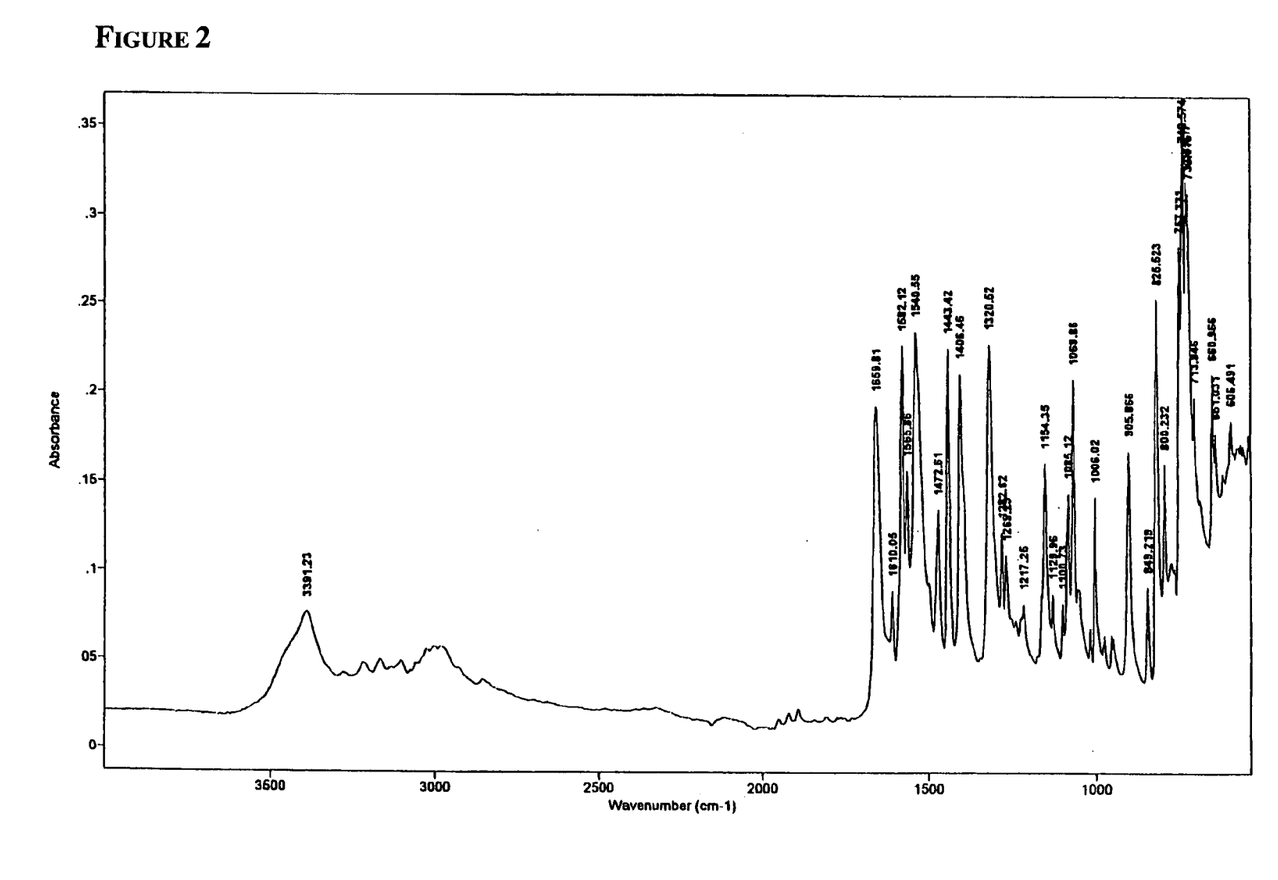
FIG. 2: IR spectrum of 2-chloro-N-(4'-chlorobiphenyl-2-yl)nicotinamide anhydrate (4000 cm$^{-1}$ to 500 cm$^{-1}$)
Figure 3:
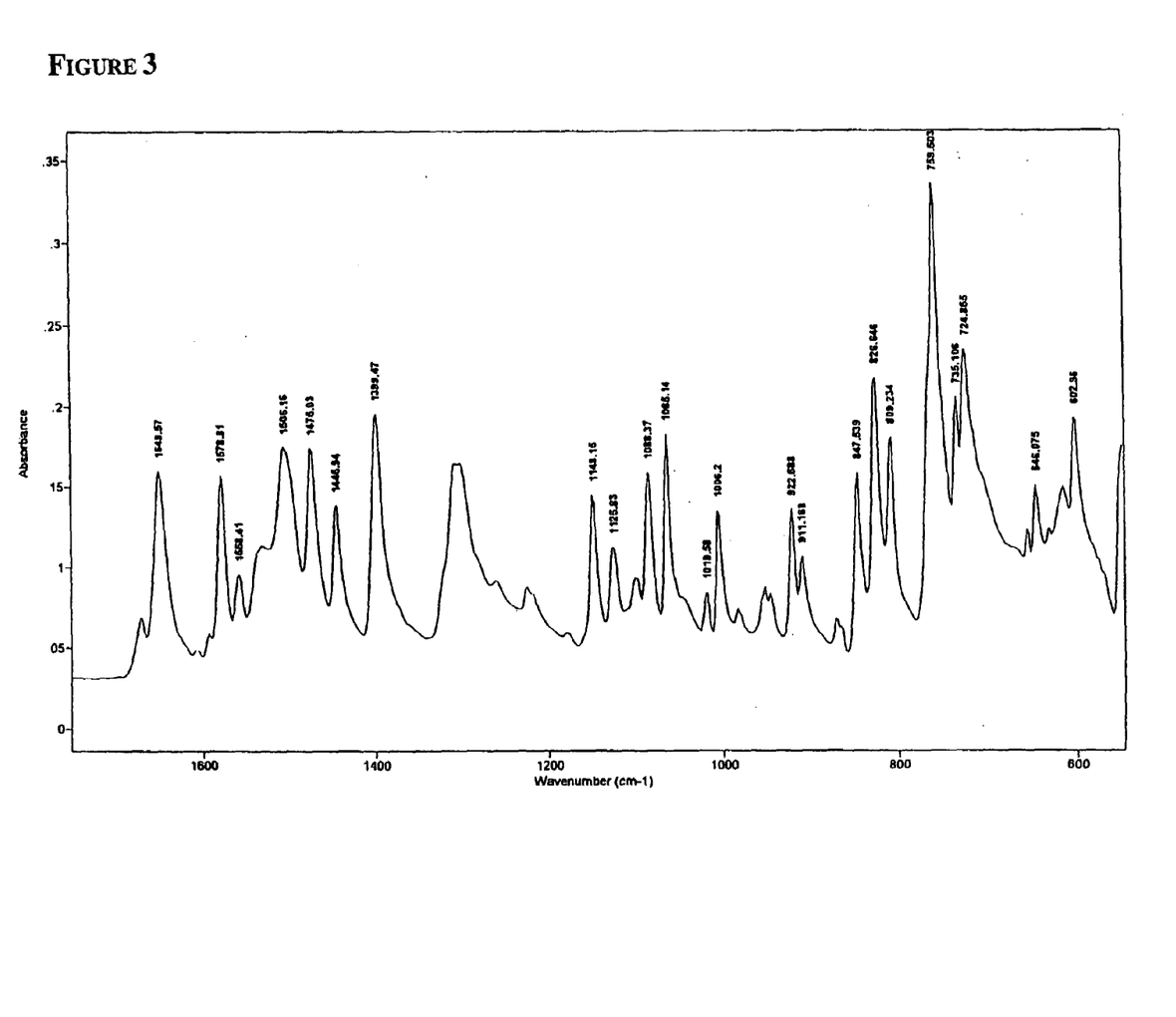
FIG. 3: IR spectrum of 2-chloro-N-(4'-chlorobiphenyl-2-yl)nicotinamide monohydrate (1800 cm$^{-1}$ to 600 cm$^{-1}$)
Figure 4:
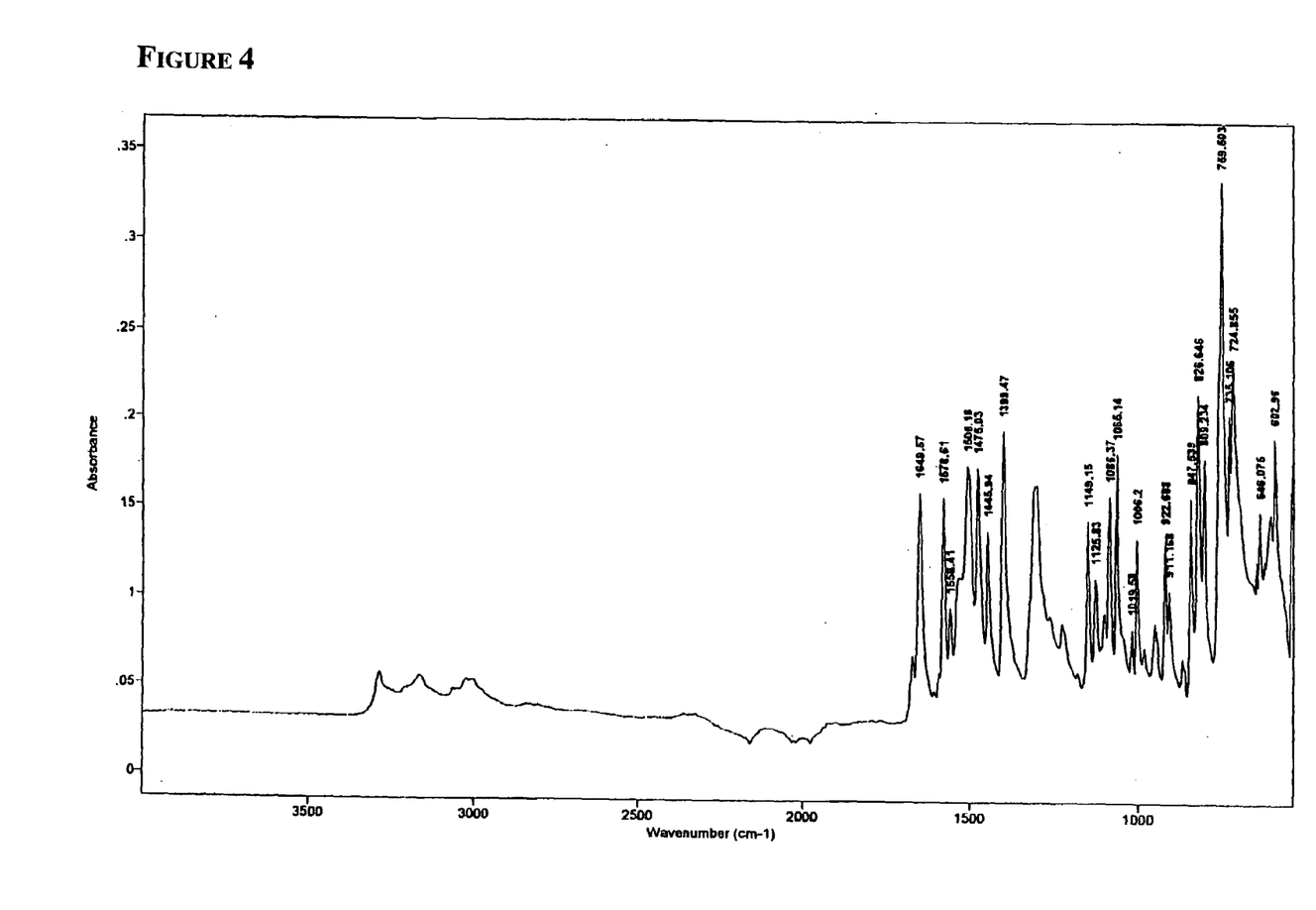
FIG. 4: IR spectrum of 2-chloro-N-(4'-chlorobiphenyl-2-yl)nicotinamide monohydrate (4000 cm$^{-1}$ to 500 cm$^{-1}$)
Figure 5:
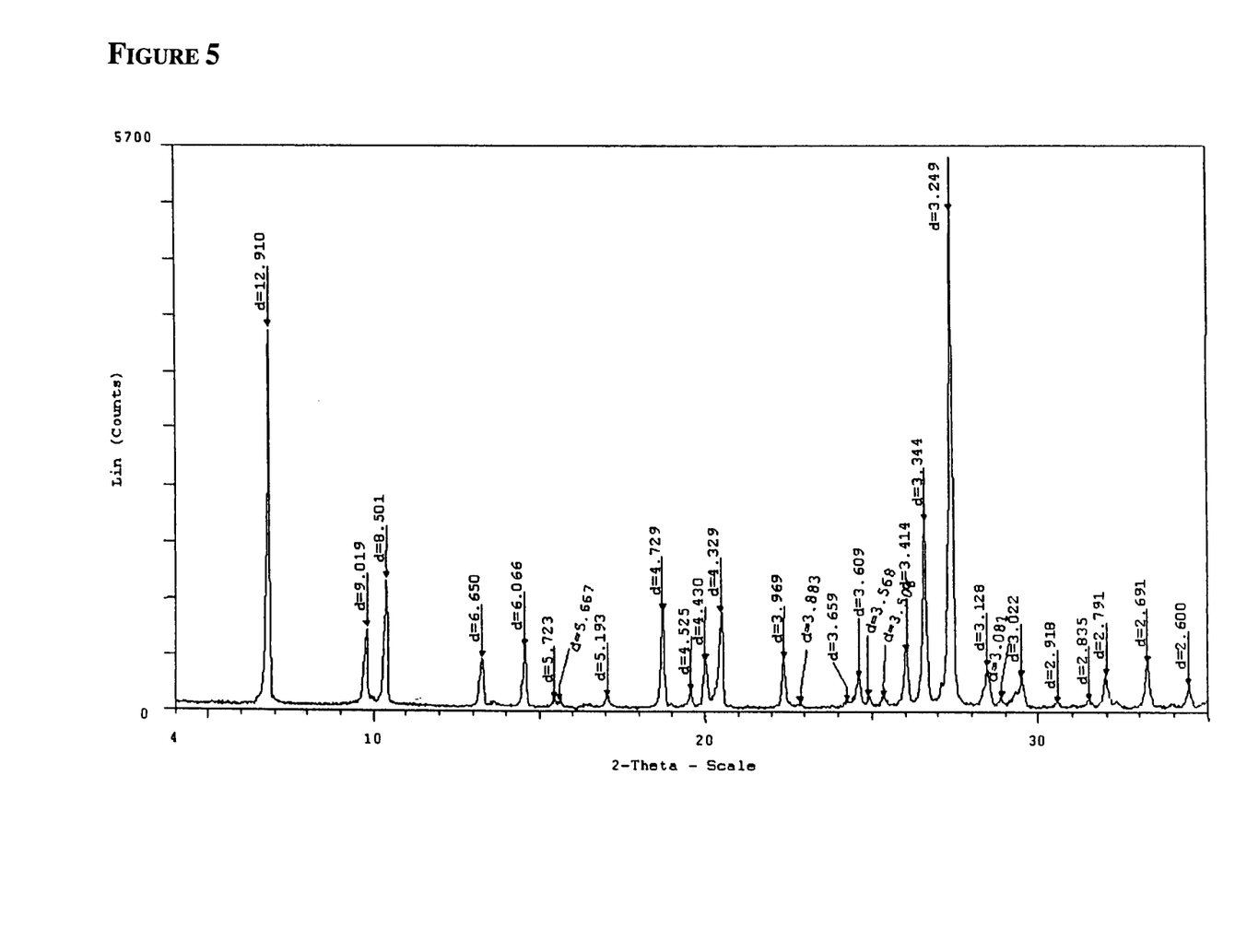
FIG. 5: X-ray powder diffractogram of 2-chloro-N-(4'-chlorobiphenyl-2-yl)nicotinamide monohydrate [conditions: step: 0.020°–step time: 4.5 s–WL1: 1.54056–temp.: 25° C. (room)]
Figure 6:
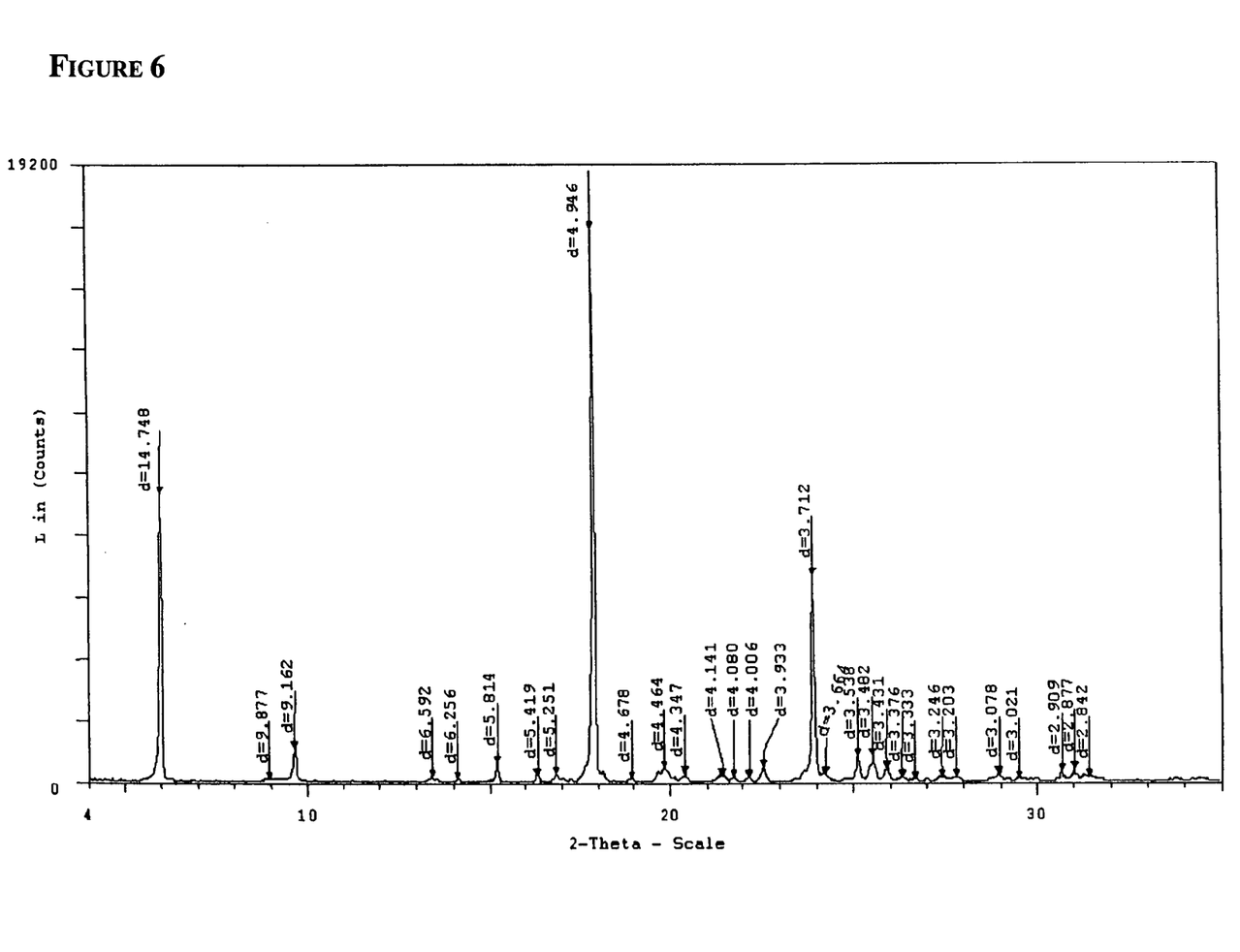
FIG. 6: X-ray powder diffractogram of 2-chloro-N-(4'-chlorobiphenyl-2-yl)nicotinamide anhydrate [conditions: step: 0.020°–step time: 4.5 s–WL1: 1.54056–temp.: 25° C. (room)]

The X-ray powder diagrams shown in FIGS. 5 to 6 (see also Table 1) were recorded using standard methods as are described, for example, in H. P. Klug and L. E. Alexander, X-Ray Diffraction Procedures (1974) or R. Jenkins and R. L. Snyder, X-Ray Powder Diffractometry (1996). The measurements were carried out with Cu-Kα radiation in a Siemens D-5000 diffractometer in the range of diffraction angles 2θ=4°–35° at a step size of 0.02°.

TABLE 1

|  | Anhydrate $[C_{18}H_{12}Cl_2N_2O]$ | Hydrate $[C_{18}H_{14}Cl_2N_2O_2]$ |
|---|---|---|
| Molar weight | 343.2 g/mol | 361.2 g/mol |
| Melting point (DSC) | 145.2° C. | endotherm 80–92° C. further peak at 145.2° C. |
| Density | 1.42 g/mol | 1.43 g/mol |
| X-ray reflection (2θ degree) Cu—Kα | 18; 22.5; 9.5; 6 | 27.2; 18.5; 10.5; 7 |
| IR absorption | 1650 cm$^{-1}$ | 1660 cm$^{-1}$, 3991 cm$^{-1}$, 800 cm$^{-1}$, |
| Water content | <1% | 5% |

EXAMPLE 2

The trade names of the adjuvants used for formulating the hydrate/anhydrate of Example 1 are compiled in Table 2.

TABLE 2

| Name | Chemical name | Source |
|---|---|---|
| Silikon ® SRE | Silicone oil emulsion | Wacker Chemie |
| Wettol ® D1 | Condensate of phenol-sulfonic acid, urea and formaldehyde | BASF Aktiengesellschaft |
| Pluronic ® PE 10500 | EO/PO block copolymer | BASF Aktiengesellschaft |
| Proxel ® GXL | Aqueous dipropylene glycol solution comprising 20% 1,2-benzoisothiazolin-3-one | ICI |

A) Formulations of the Anhydrate 500 g of 2-chloro-N-(4'-chlorobiphenyl-2-yl)nicotinamide anhydrate were added to a mixture of 30 g of Wettol D1, 40 g of Pluronic PE 10500, 4 g of Proxel GXL, 50 g of propylene glycol and 5 g of Silikon SRE in approx. 300 ml of water. After the mixture had been stirred briefly, it was pumped through a Dyno KDL mill (1.2 mm beads, milling space 1.2 l) at a rate of 2 l/h. After only a short time, the mill became clogged and had to be switched off. The suspension collected in the receiver also started to solidify.

B) Formulations of the Hydrate 500 g of 2-chloro-N-(4'-chlorobiphenyl-2-yl)nicotinamide monohydrate were combined as described under A with adjuvants. After the mixture had been stirred briefly, it was pumped through a Dyno KDL mill (1.2 mm beads, milling space 1.2 l) at a rate of 2 l/h. The milling process was carried out without problems. No clogging of the mill or crystallization in the receiver was observed. After eight milling passes, a sufficiently fine particle size of 70%<2 μm (Malvern Mastersizer) was achieved, i.e. the particle diameter of 70% of the particles is <2 μm.

C) Characterization and Comparison of the Resulting Formulations

While the procedure described under Example 2 A) gave a loamy crystal slurry even before the preparation was complete (formulation A) which had to be discarded, the process described under B) (formulation B) gave a storage-stable formulation in which no further crystallization was observed.

The particle size of the resulting formulation B was measured using a Malvern Mastersizer (see Table 3). The data shown are the percentage of the particles which are smaller than 2 μm.

TABLE 3

|  | After 0 h | After 1 month [20° C.] | After 6 months [20° C.] | After 1 month [40° C.] |
|---|---|---|---|---|
| Particle diameter [ % < 2 μm] | 79 | 79 | 79 | 75 |

EXAMPLE 3

Preparation of the Hydrate by Direct Conversion

A) Mechanical Method 25 kg of 2-chloro-N-(4'-chlorobiphenyl-2-yl)nicotinamide anhydrate are added to a mixture of 1.5 kg of Wettol® D1, 2 kg of Pluronic®PE 10500, 200 g of Proxel® GXL, 2.5 kg of propylene glycol and 250 g of Silikon®SRE in approx. 15 l of water.

For conversion into the hydrate, the mixture was passed repeatedly throught a rotor-stator mill of type PuC (gap width 0.2 mm, throughput 200–300 l/h). After each pass, the degree of conversion of the anhydrate into the hydrate was monitored by IR spectroscopy. The conversion was complete after 4 to 7 passes. The subsequent fine-milling by Dyno mill was carried out without problems. Storage-stable goods complying with specification were obtained.

B) Thermal Method

In a heatable stirred vessel, 25 kg of 2-chloro-N-(4'-chlorobiphenyl-2-yl)nicotinamide anhydrate are mixed as described in the mixing specification 3 A) with adjuvants and water. The mixture was stirred for 5 hours at 50° C. using a propeller mixer. An IR spectroscopy check revealed that complete conversion into the hydrate had taken place during this period. After cooling to 30° C., the product was milled in a stirred ball mill (Dyno type); after 8 passes at a throughput of 100 l/h, product complying with specification was obtained.

We claim:

1. A crystalline hydrate of a substituted anilide derivative of the formula I in which
A is $R^1$ is phenyl which is substituted by halogen,
$R^2$ is methyl, difluoromethyl, trifluoromethyl, chlorine, bromine or iodine,
$R^3$ is trifluoromethyl or chlorine.

2. A hydrate as claimed in claim 1 in the form of the monohydrate.

3. A method for the preparation of a hydrate as claimed in claim 1 or 2, comprising the following steps:
   a) dissolving the anhydrate of I in a water-soluble organic solvent, and
   b) precipitating the hydrate of I by addition of water.

4. A method as claimed in claim 3, wherein the organic solvent used is dioxane, tetrahydrofuran, dimethylformamide or N-methylpyrrolidone or mixtures of these.

5. A method for the preparation of a hydrate as claimed in claim 1 or 2, comprising the following steps:
   a) mixing an organic solution comprising the anhydrate of I with water,
   b) heating the mixture prepared in step a) at a temperature of 30–150° C.,
   c) cooling the resulting solution.

6. A method as claimed in claim 5, wherein the organic solvent used is benzene, toluene, xylene, tetrahydrofuran, dimethylformamide or N-methylpyrrolidone or mixtures of these.

7. A method for the preparation of a hydrate as claimed in claim 1 or 2, comprising the following steps:
   a) mixing the solid anhydrate of I with water,
   b) heating the mixture prepared in step a) at a temperature of 30–150° C. until the anhydrate has been converted into the hydrate, or
   c) incubating of the mixture prepared in step a) with exposure to shearing forces until the anhydrate has been converted into the hydrate.

8. A method as claimed in any of claims 5 to 7, where the mixture prepared in step a) is mixed with formulation auxiliaries.

9. A method as claimed in claim 5, wherein the solution prepared in step a) is incubated at a temperature of 30–70° C.

10. A suspension concentrate comprising, as essential component, the hydrate as claimed in claim 1 or 2.

11. A multiphase suspoemulsion comprising, as essential component, the hydrate as claimed in claim 1 or 2.

12. A method of controlling phytopathogenic fungi, which comprises diluting a suspension concentrate as claimed in claim 10 or a multiphase aqueous suspoemulsion as claimed in claim 11 and applying the solution to the pest in question or to the materials, plants, soil and seeds to be protected from the pest in question.

13. A method as claimed in claim 12, wherein the suspension concentrate or the suspoemulsion comprises in each case at least one further fungicidal active ingredient.

14. A method for the control of phytopathogenic fungi and the simultaneous control of undesired attack by insects or mites and/or for regulating the growth of plants, which comprises diluting a suspension concentrate as claimed in claim 10 or a multiphase aqueous suspoemulsion as claimed in claim 11 and applying the dilute product to the pest in question or to the materials, plants, soil and seeds to be protected from the pest in question, it being possible for the suspension concentration or the suspoemulsion to comprise in each case at least one further agrochemical active ingredient.

* * * * *